(12) United States Patent
Rebbaa et al.

(10) Patent No.: US 9,649,300 B2
(45) Date of Patent: May 16, 2017

(54) INHIBITION OF WNT, TGF BETA AND HIPPO SIGNALING PATHWAYS TO TREAT CANCER, ORGAN FIBROSIS AND METABOLIC DISORDERS

(71) Applicants: University of Pittsburgh—of the Commonwealth System of Higher Education, Pittsburgh, PA (US); Chatham University, Pittsburgh, PA (US)

(72) Inventors: Abdelhadi Rebbaa, Northvale, NJ (US); Robert B. Lettan, II, Pittsburgh, PA (US)

(73) Assignees: University of Pittsburgh—Of the Commonwealth System of Higher Education, Pittsburgh, PA (US); Chatham University, Pittsburgh, PA (US)

( * ) Notice: Subject to any disclaimer, the term of this patent is extended or adjusted under 35 U.S.C. 154(b) by 0 days.

(21) Appl. No.: 14/915,188

(22) PCT Filed: Aug. 19, 2014

(86) PCT No.: PCT/US2014/051714
§ 371 (c)(1),
(2) Date: Feb. 26, 2016

(87) PCT Pub. No.: WO2015/031109
PCT Pub. Date: Mar. 5, 2015

(65) Prior Publication Data
US 2016/0200697 A1 Jul. 14, 2016

Related U.S. Application Data

(60) Provisional application No. 61/871,186, filed on Aug. 28, 2013.

(51) Int. Cl.
C07D 285/10 (2006.01)
A61K 45/06 (2006.01)
A61K 31/433 (2006.01)

(52) U.S. Cl.
CPC .......... A61K 31/433 (2013.01); A61K 45/06 (2013.01); C07D 285/10 (2013.01)

(58) Field of Classification Search
None
See application file for complete search history.

(56) References Cited

U.S. PATENT DOCUMENTS

| 4,555,521 A * | 11/1985 | Engel ............... A01N 43/82 514/362 |
|---|---|---|
| 2011/0027186 A1 | 2/2011 | Hong et al. |
| 2012/0238562 A1 | 9/2012 | Cinar et al. |

OTHER PUBLICATIONS

Bao et al., "A cell-based assay to screen stimulators of the Hippo pathway reveals the inhibitory effect of dobutamine on the YAP-dependent gene transcription," *J. Biochem.*, 150(2): 199-208, May 17, 2011.
Fogarty et al., "Development of protein kinase activators: AMPK as a target in metabolic disorders and cancer," *Biochimica et Biophysica Acta*, 1804(3): 581-591, Mar. 2010.
International Search Report and Written Opinion issued in International Application No. PCT/US2014/051714, Dec. 17, 2014.

* cited by examiner

*Primary Examiner* — Yong Chu
(74) *Attorney, Agent, or Firm* — Klarquist Sparkman, LLP

(57) ABSTRACT

Compounds, or pharmaceutically acceptable salts or esters thereof, having a structure of:

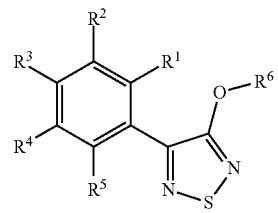

wherein each of $R^1$-$R^5$ is individually selected from H, halogen, optionally substituted alkyl, optionally substituted alkoxy, nitro, sulfonamide, hydroxy, or amino; and $R^6$ is selected from H, optionally substituted alkyl, or optionally substituted aryl.

14 Claims, 11 Drawing Sheets

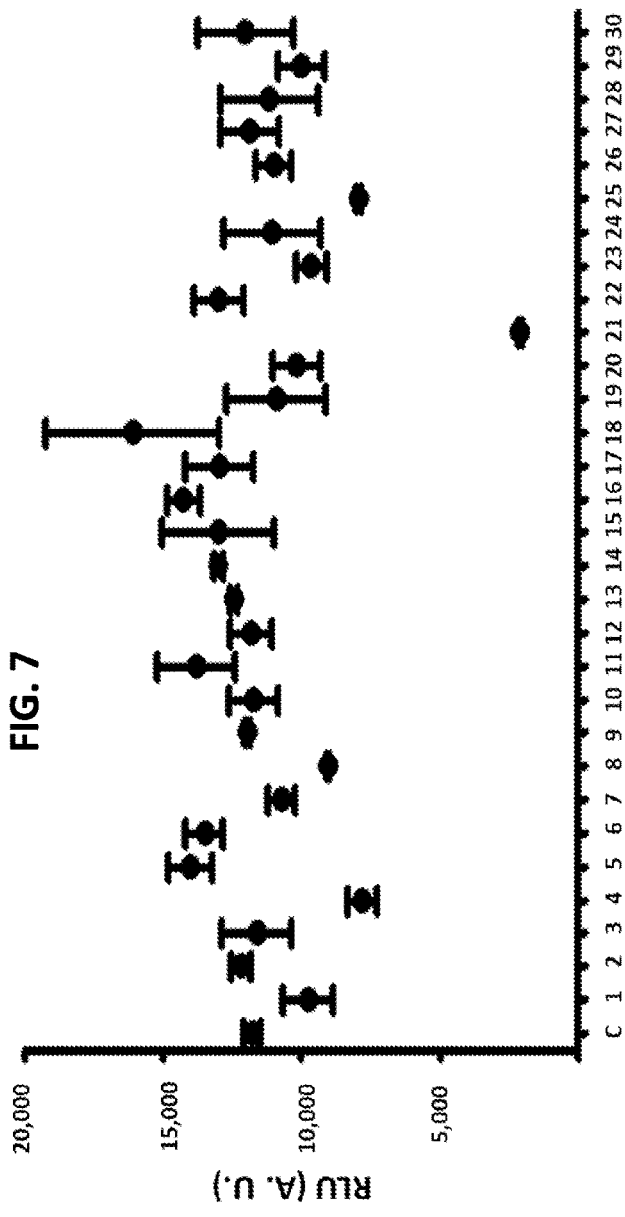

FIG. 7

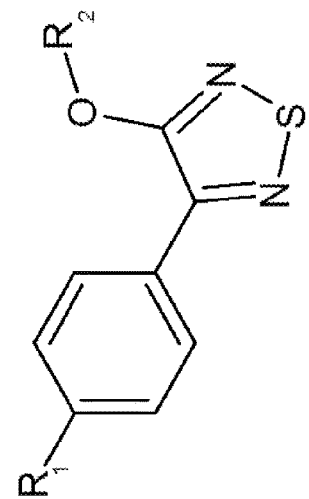

1. R1=H, R2=H; 2- R1=H, R2=Ph; 3- R1=H, R2=Ph-Me; 4-R1=H, R2=Ph-CH2-CH3; 5- R1=H, R2=Ph-CH2-CH2OH; 6- R1=Cl, R2=H; 7- R1=Cl, R2=Ph; 8- R1=Cl, R2=Ph-Me; 9-R1=Cl, R2=Ph-CH2-CH3; 10-R1=Cl, R2=Ph-CH2-CH2OH; 11-R1=CH3, R2=H; 12- R1=CH3, R2=Ph; 13- R1=CH3, R2=Ph-Me; 14-R1=CH3, R2=Ph-CH2-OH; 15- R1=CH3, R2=Ph-CH2-CH2OH; 16- R1=Cl, R2=H; 17- R1=Cl, R2=Ph;18- R1=Cl, R2=Ph-Me; 19- R1=Cl, R2=-CH2-CH2-OH; 20- R1=Cl, R2=-CH2-CH2-CH2OH; 21-R1=Cl, R2=-CH2-CH2-CH2-OH;22- R1=Cl, R2=-CH2-CH2-CH2-CH2-OH; 23-R1=H, R2=-CH2-CH2-OH; 24- R1=H, R2=-CH2-CH2-CH2-CH2-OH; 25-R1=H, R2=-CH2-CH2-CH2-CH2-OH; 26- R1=OCH3, R2=H; 27- R1=OCH3, R2=Ph; 28- R1=OCH3, R2=Ph-Me; 29-R1=OCH3, R2=CH2-CH2-OH; 30-R1=OCH3, R2=-CH2-CH2-CH2-OH

FIG. 8
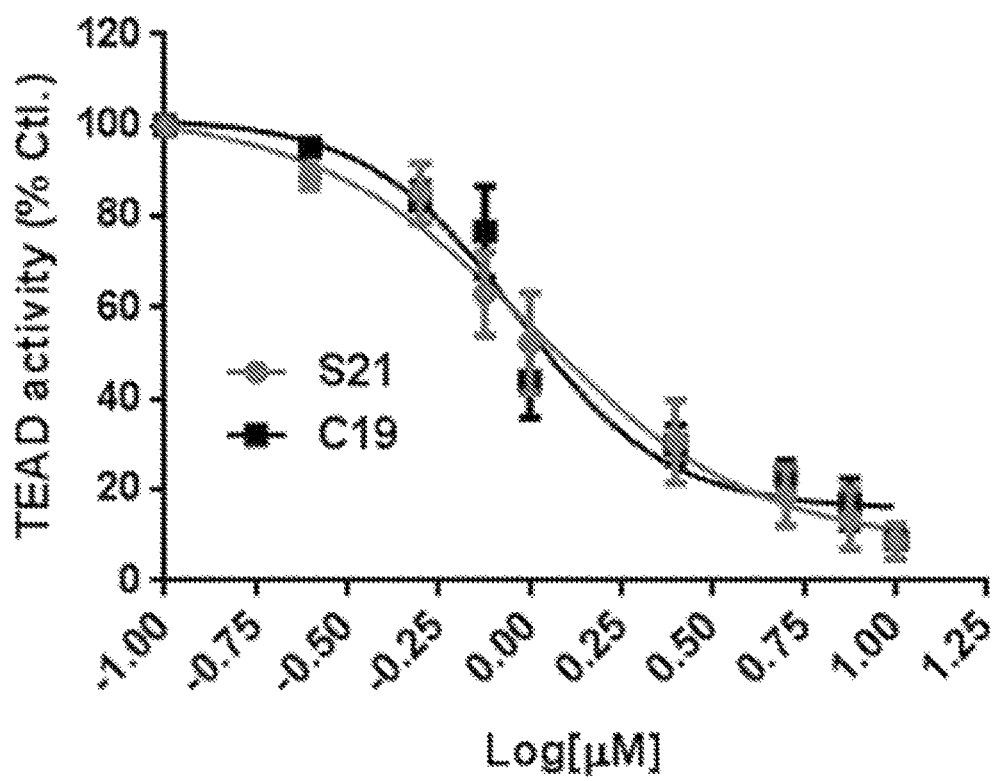
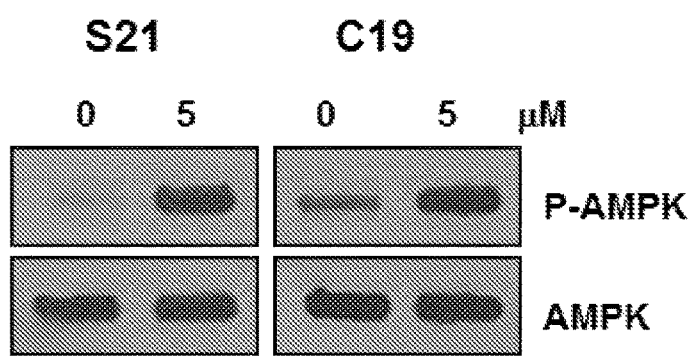

Figure 2. Effect of C19 (mg/Kg) on tumor growth (Panel A) and body weight (Panel B). Data represents of 7 replicates ±SE. * $p<0.05$, ** $p<0.01$.

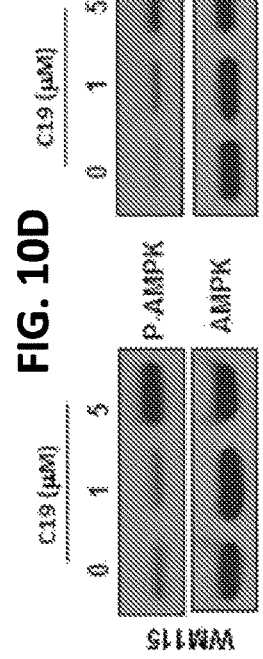
FIG. 10D
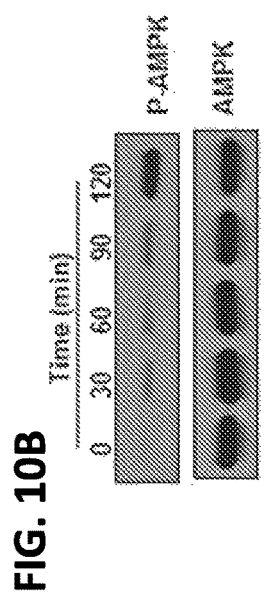
FIG. 10E
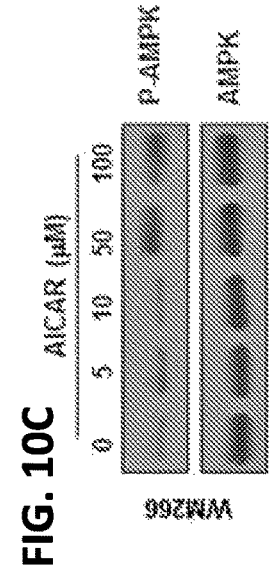
FIG. 10F
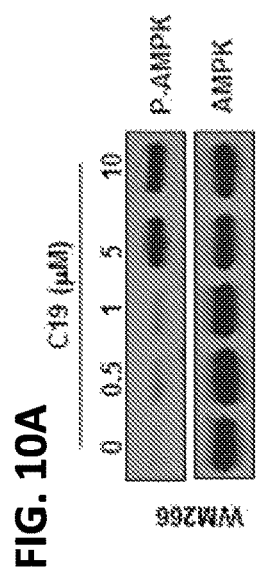
FIG. 10A
FIG. 10B
FIG. 10C

INHIBITION OF WNT, TGF BETA AND HIPPO SIGNALING PATHWAYS TO TREAT CANCER, ORGAN FIBROSIS AND METABOLIC DISORDERS

RELATED APPLICATION

This application is at National Stage Application of PCT/US2014/051714, filed Aug. 1, 2014, which in turn claims the benefit of U.S. Provisional Application No. 61/871,186, filed on Aug. 28, 2013, which is are incorporated by reference herein in its entirety.

BACKGROUND

Epithelial-mesenchymal transition (EMT) is a transdifferentiation process by which epithelial cells undergo changes in morphology and cell-cell junction, to detach from each other and acquire invasive abilities. EMT is recognized to play key roles in processes such as wound healing, tissue fibrosis and cancer. With regard to cancer, EMT not only allows cancer cells to disseminate from the primary tumor but also confers protection from cell death, facilitates immune escape and induces resistance to therapy. TGF beta and Wnt signaling are considered the major drivers of EMT, however recent findings indicated that both of these pathways are regulated by a third one named Hippo. In fact, downstream mediators of this pathway namely YAP, TAZ and TEAD were found to act independently or as co-activators for both beta catenin/TCF and Smad complexes to induce EMT. Based on this, the development of approaches to inhibit activity of the Hippo pathway is expected to have applications for the treatment of EMT-associated diseases.

The adenosine monophosphate-activated protein kinase (AMPK) is an important regulatory protein for cellular energy balance and is considered a master switch of glucose and lipid metabolism in various organs, especially in skeletal muscle and liver. Recent evidence indicated that the function of this enzyme extends beyond the canonical metabolic pathway to include tumor suppression, cell polarity, fibrosis, and even aging. Concerning its role in metabolism, AMPK was originally defined as the upstream kinase for the critical metabolic enzymes Acetyl-CoA carboxylase (ACC1 & ACC2) and HMG-CoA reductase, which serve as the rate limiting steps for fatty-acid and sterol synthesis in a wide-variety of eukaryotes. In specialized tissues such as muscle and fat, AMPK regulates glucose uptake via the RabGAP TBC1D1, which along with its homolog TBC1D4 (AS160), play key roles in GLUT4 trafficking following exercise and insulin. In skeletal muscles, AMPK stimulates glucose transport and fatty acid oxidation, and in the liver, it augments fatty acid oxidation and decreases glucose output, cholesterol and triglyceride synthesis. These metabolic effects induced by AMPK are associated with lowering blood glucose levels in hyperglycemic individuals.

In conditions where nutrients are scarce, AMPK acts as a metabolic checkpoint inhibiting cellular growth. The most thoroughly described mechanism by which AMPK regulates cell growth is via suppression of the mammalian target of rapamycin complex 1 (mTORC1) pathway. This occurs by direct phosphorylation of the tumor suppressor TSC2 and also through direct phosphorylation of Raptor (regulatory associated protein of mTOR), on two conserved serines, which blocks the ability of the mTORC1 kinase complex to phosphorylate its substrates. mTORC1 has been shown to induce cell growth through inhibition of autophagy, a cellular process of "self engulfment" in which the cell breaks down its own organelles (macroautophagy) and cytosolic components (microautophagy) to ensure sufficient metabolites when nutrients run low. In addition to inhibitory phosphorylation of mTORC1, studies from a number of laboratories in the past few years have revealed that AMPK directly activates the ULK1, a kinase with a critical role in autophagy and mitochondrial homeostasis.

AMPK has also been shown to mediate the tumor suppressive function of the liver kinase LKB1, a gene associated with Peutz-Jeghers syndrome, an autosomal dominant genetic disorder characterized by multiple hamartomatous polyps (benign overgrowth of differentiated tissues) in the gastrointestinal tract and a markedly increased risk of gastrointestinal adenocarcinomas, of lung adenocarcinomas, 19% of squamous cell carcinomas and 20% of cervical carcinomas and other cancers In addition to the well-established role for AMPK in cell growth and metabolism, recent studies suggested that AMPK may control cell polarity and cytoskeletal dynamics. In fact, it has been known for some time that the AMPK upstream effector, LKB1 plays a critical role in cell polarity from simpler to complex eukaryotes. These studies also supported a role for AMPK in cell polarity as a loss of this enzyme in *Drosophila* results in altered polarity and its activation in mammalian MDCK cells was needed for proper re-polarization and tight junction formation.

Loss of cell polarity is a consequence of epithelial mesenchymal transition (EMT). During this process epithelial cells lose their intercellular connections (tight junctions and adherens junction), change morphology and separate from each other. The affected cells generally adopt a spindly (elongated) morphology that facilitates their migration to distant sites. EMT has been shown to play key roles in development, cancer and organ fibrosis. AMPK has been shown to exert its inhibitory effect on renal fibrosis induced by TGF-$\beta$, angiotensin II, aldosterone, and high glucose, principally through inhibition of EMT. Moreover, the AMPK activator Metformin also suppresses EMT and thiazolidinediones were found to improve hepatic fibrosis by activating the AMPK signaling pathway in rats with non-alcoholic steatohepatitis. AMPK also plays a role in cardiac remodeling, as it pertains to diabetic cardiomyopathy, cardiac hypertrophy, and heart failure, suggesting that there might be therapeutic value in targeting the AMPK signaling pathway to treat cardiovascular diseases. In fact, dysfunction of the AMPK signaling pathway has been shown to be involved in the genesis and development of various cardiovascular diseases, including atherosclerosis, hypertension and stroke. AMP-activated protein kinase activator AICAR acutely lowers blood pressure and relaxes isolated resistance arteries of hypertensive rats. Adiponectin, a hormone AMPK activator has been shown to inhibit doxorubicin-induced cardiotoxicity.

In addition to its well established role in metabolism, cancer and fibrosis, AMPK has also been shown to affect other aging-associated diseases such as inflammation, neurodegeneration, sarcopenia and even the aging process itself. This is exemplified by the findings that the AMPK activator AICAR inhibits TNF-a- and IL-1a-induced NF-B reporter gene expression dose dependently in immune cells and inducible nitric oxide synthase and cyclooxygenase-2 (COX-2) expression in stimulated macrophages. Activators of AMPK were also reported to inhibit chemotaxis in the monocyte-like cell line U937. In addition, AICAR profoundly inhibited lipopolysaccharide and IFN-$\alpha$-stimulated production of the proinflammatory molecules nitric oxide synthase, COX-2, and IL-6. With regard to neurodegeneration, emerging studies indicate that AMPK signaling can regulate tau protein phosphorylation and amyloidogenesis, the major hallmarks of AD. AMPK is also a potent activator of autophagic degradation which seems to be suppressed in AD.

Sarcopenia is characterized by a muscle atrophy (a decrease in the size of the muscle), along with a reduction in muscle tissue "quality," caused by such factors as replacement of muscle fibers with fat, an increase in fibrosis, changes in muscle metabolism, oxidative stress, and degeneration of the neuromuscular junction. Combined, these changes lead to progressive loss of muscle function and frailty. Agents that activate AMPK such as AICAR and GW501516 induced improvements in disease phenotype, including an increase in overall behavioral activity and significant gains in forelimb and hind limb strength.

Many studies with lower organisms have revealed that increased AMPK activity can extend the lifespan. Experiments in mammals have demonstrated that AMPK controls autophagy through mTOR and ULK1 signaling which augment the quality of cellular housekeeping. Moreover, AMPK-induced stimulation of FoxO/DAF-16, Nrf2/SKN-1, and SIRT1 signaling pathways and improves cellular stress resistance. Emerging studies indicate that the responsiveness of AMPK signaling clearly declines with aging. The loss of sensitivity of AMPK activation to cellular stress impairs metabolic regulation, increases oxidative stress and reduces autophagic clearance. These age-related changes activate immune cells, triggering a low-grade inflammation and metabolic disorders, leading to acceleration of aging. In contrast, evidence was provided that chronic feeding of rodents with AMPK agonists improves muscle endurance, reduces metabolic diseases, allows proper circadian regulation, and suppresses tumorigenesis. These findings strengthen AMPK's position as a main beacon of hope for the prevention and/or treatment of the current epidemic of metabolic and age-related diseases.

AMPK is generally activated in response to nutrient deprivation, exercise and also by hormones such as leptin, grelin, and adiponectin. Two classes of oral antihyperglycemic drugs (biguanidines and thiazolidinediones) have been shown to exert some of their therapeutic effects by directly or indirectly activating AMPK. Novel pharmacological agents such as the prototypical activator 5-aminoimidazole-4-carboxamide 1-D-ribonucleoside (AICAR) and Abbott A769662 have recently been introduced. Interestingly, oral administration of AICAR to eight-week-old male C57B/6J mice was reported to mediate a 44% increase in endurance without exercise in untrained mice, leading to speculation that these type of compounds may be considered as exercise mimetics. However, side effects and an acquired resistance to these drugs emphasize the need for the development of novel and efficacious AMPK activators.

SUMMARY

Disclosed herein are compounds, or pharmaceutically acceptable salts or esters thereof, having a structure of:

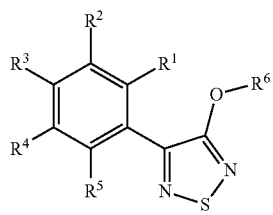

wherein each of $R^1$-$R^5$ is individually selected from H, halogen, optionally substituted alkyl, optionally substituted alkoxy, nitro, sulfonamide, hydroxy, or amino; and $R^6$ is selected from H, optionally substituted alkyl, or optionally substituted aryl.

Also disclosed herein is a method for treating an epithelial-mesenchymal transition-associated disorder or an adenosine monophosphate-activated protein kinase-associated disorder in a subject, comprising administering to the subject in need thereof a therapeutically effective amount of a compound disclosed herein.

Further disclosed herein is a method of inhibiting at least one of a Hippo, Wnt, and TGF beta pathway in a subject, comprising administering to the subject a compound as disclosed herein.

Additionally disclosed herein is a method of inhibiting an epithelial-mesenchymal transition in a cell, comprising contacting the cell with a compound disclosed herein.

Also disclosed herein is a method of activating an adenosine monophosphate-activated protein kinase in a cell, comprising contacting the cell with a compound disclosed herein.

The foregoing will become more apparent from the following detailed description, which proceeds with reference to the accompanying figures.

BRIEF DESCRIPTION OF THE DRAWINGS

FIG. 1A. Hippo associated luciferase reporter (8xGT-II) was used to screen a series of 30 thiadiazole derivatives. Cells transfected with the construct were incubated in the absence (c) or presence of the compounds at 10 µM for 24 hours. Luciferase activity expressed in arbitrary units (AU) was measured in protein extracts. Data represent average for three replicates ±SE. FIG. 1B. Structure of S21 compound. FIG. 1C. Activity of S21 on Hippo versus CMV-Luciferase reporter measured as described above.

FIG. 4A. Western blots showing inhibition of various EMT genes in melanoma cells WM266 exposed to the indicated concentrations of S21 for 24 hours. FIG. 4B. Cell monolayer scratch assay depicting inhibition of cell migration by S21. FIG. 4C. Effect of S21 on cell proliferation measured after 5 days of incubation. FIG. 4D. Cell response to doxorubicin was measured in the presence of and absence of S21. Data in panels C and D represent average of three determinations ±SE.

FIG. 6A. QPCR analysis depicting expression levels of pro-EMT ad fibrosis genes in the absence and the presence of S21. FIG. 6B. Western blot analysis showing the effect of S21 on expression of fibronectin, collagen and vimentin. Beta catenin was used as a loading control.

FIG. 7 shows the structures of the compounds screened in FIG. 1A.

FIG. 8 shows the inhibition of Hippo signaling and activation of AMPK by S21 and C19.

FIGS. 10A-10F. FIGS. 10A and 10B. Dose and time dependent effects of C19 on phosphorylation of AMPK. In FIG. 10B, C19 was used at 5 µM. FIG. 10C. Effect of AICAR on phosphorylation of AMPK. FIG. 10D. Confirmation in different cell lines. FIGS. 10E and 10F. Effect of C19 on phosphorylation of downstream AMPK targets ACC and UIK1.

DETAILED DESCRIPTION

Terminology

Figure 1A:
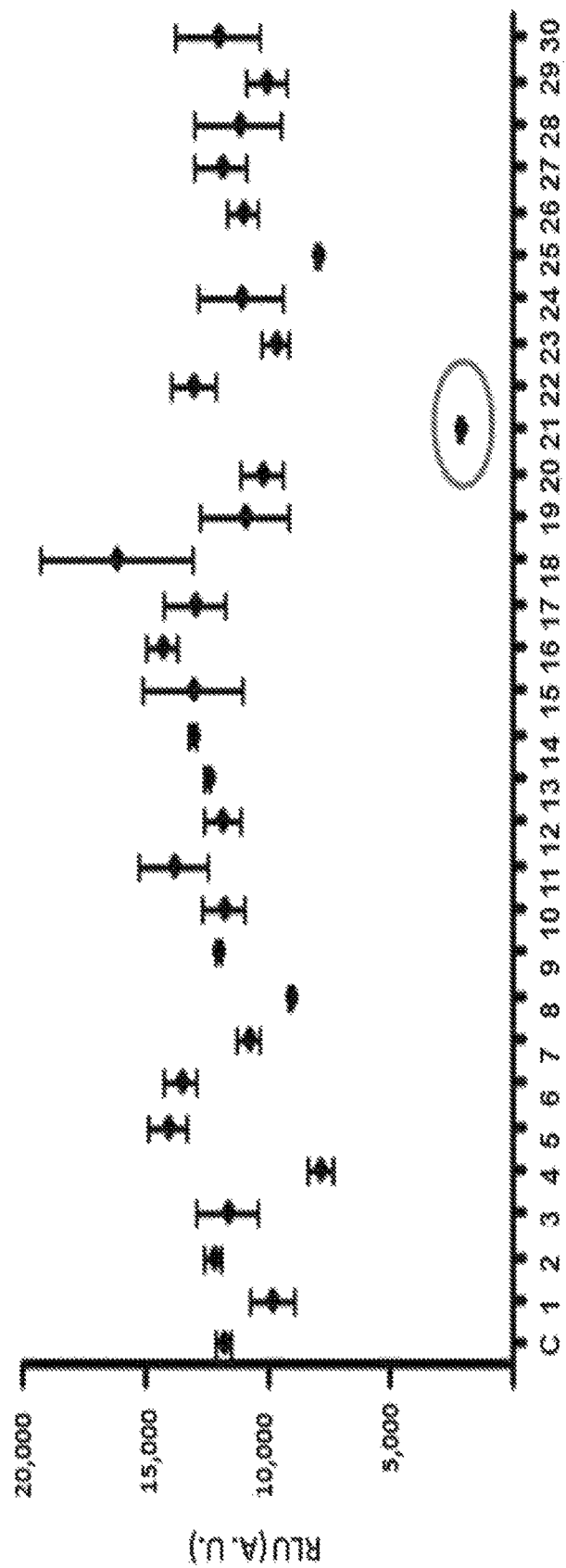
FIGS. 1A-1C. Screening for small molecules inhibitors of the Hippo pathway.
Figure 1C:
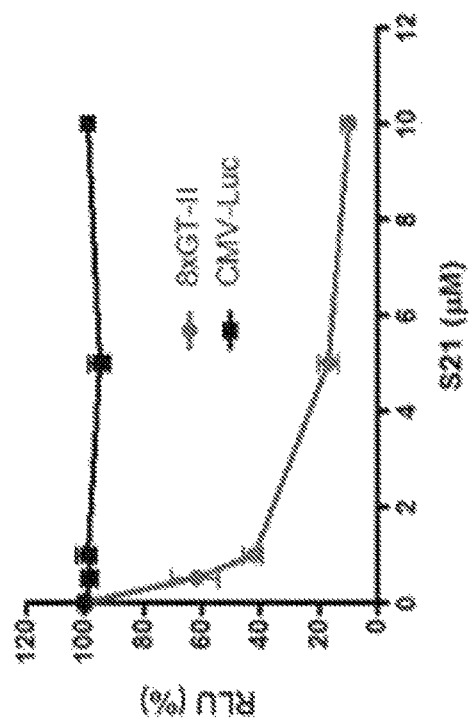
Figure 1B:
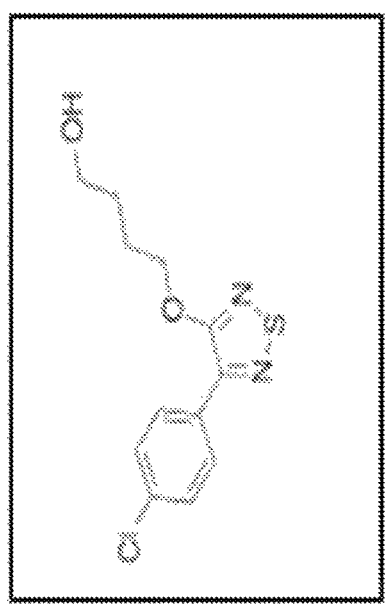

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Administration" as used herein is inclusive of administration by another person to the subject or self-administration by the subject.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula—OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, isobutoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl;$(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy.

The term "amine" or "amino" refers to a group of the formula —NRR', where R and R' can be, independently, hydrogen or an alkyl, alkenyl, alkynyl, aryl, aralkyl, cycloalkyl, halogenated alkyl, heterocycloalkyl or other substituted group. For example, an "alkylamino" or "alkylated amino" refers to —NRR', wherein at least one of R or R' is an alkyl.

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R', where R and R' independently can be a hydrogen, alkyl, alkenyl, alkynyl, aryl, aralkyl, cycloalkyl, halogenated alkyl, heterocycloalkyl group or other substituted group. A suitable aminocarbonyl group is acetamido.

The term "amide" or "amido" is represented by the formula —C(O)NRR', where R and R' independently can be a hydrogen, alkyl, alkenyl, alkynyl, aryl, aralkyl, cycloalkyl, halogenated alkyl, heterocycloalkyl group or other substituted group.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Aryl" refers to a monovalent unsaturated aromatic carbocyclic group having a single ring (e.g., phenyl) or multiple condensed rings (e.g., naphthyl or anthryl), which can optionally be unsubstituted or substituted. A "heteroaryl group," is defined as an aromatic group that has at least one heteroatom incorporated within the ring of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

The term "aralkyl" refers to an alkyl group wherein an aryl group is substituted for a hydrogen of the alkyl group. An example of an aralkyl group is a benzyl group.

"Aryloxy" or "heteroaryloxy" refers to a group of the formula —OAr, wherein Ar is an aryl group or a heteroaryl group, respectively.

The term "co-administration" or "co-administering" refers to administration of a dendrimeric compound disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks.

The term "ester" refers to a carboxyl group having the hydrogen replaced with, for example, a $C_{1-6}$alkyl group ("carboxyl$C_{1-6}$ alkyl" or "alkylester"), an aryl or aralkyl group ("arylester" or "aralkylester") and so on. $CO_2C_{1-3}$alkyl groups are preferred, such as for example, methylester ($CO_2Me$), ethylester ($CO_2Et$) and propylester ($CO_2Pr$) and includes reverse esters thereof (e.g. —OCOMe, —OCOEt and —OCOPr).

The term "halogen" refers to fluoro, bromo, chloro and iodo substituents.

The terms 'halogenated alkyl" or "haloalkyl group" refer to an alkyl group as defined above with one or more hydrogen atoms present on these groups substituted with a halogen (F, Cl, Br, I).

The term "hydroxyl" is represented by the formula —OH.

"Inhibiting" refers to inhibiting the full development of a disease or condition. "Inhibiting" also refers to any quantitative or qualitative reduction in biological activity or binding, relative to a control.

"Nitro" refers to an R-group having the structure —$NO_2$.

An "R-group" or "substituent" refers to a single atom (for example, a halogen atom) or a group of two or more atoms that are covalently bonded to each other, which are covalently bonded to an atom or atoms in a molecule to satisfy the valency requirements of the atom or atoms of the molecule, typically in place of a hydrogen atom. Examples of R-groups/substituents include alkyl groups, hydroxyl groups, alkoxy groups, acyloxy groups, mercapto groups, and aryl groups.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Substituted" or "substitution" refer to replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

"Sulfonamide" refers to —$SO_2NRR'$ where R and R' can be, independently, hydrogen or an alkyl, alkenyl, alkynyl, aryl, aralkyl, cycloalkyl, halogenated alkyl, or heterocycloalkyl group.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition. In certain embodiments disclosed herein, the treatment inhibits cancer or organ fibrosis.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, C.sub.1-4 alkyl, or C.sub.1-4 alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Some of the compounds described herein may also exist in their tautomeric form.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. F or a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

Groups which are substituted (e.g. substituted alkyl), may in some embodiments be substituted with a group which is substituted (e.g. substituted aryl). In some embodiments, the number of substituted groups linked together is limited to two (e.g. substituted alkyl is substituted with substituted aryl, wherein the substituent present on the aryl is not further substituted). In some embodiments, a substituted group is not substituted with another substituted group (e.g. substituted alkyl is substituted with unsubstituted aryl).

Overview

The present disclosure concerns the discovery of small molecules inhibitors of Hippo, Wnt, and TGF beta pathways. In certain embodiments, the compounds disclosed herein simultaneously inhibit Hippo, Wnt, and TGF beta pathways to treat cancer and/or organ fibrosis. These pathways are known to play critical roles in the induction of epithelial-mesenchymal transition (EMT) a cellular process responsible for cancer metastasis, resistance to therapy and organ fibrosis. Recently, both Wnt and TGF beta signalling were found to be regulated by the Hippo pathway, suggesting that targeting the latter may have a better therapeutic outcome in treating EMT-associated disorders. In a search for putative inhibitors of the Hippo pathway, a luciferase reporter system was used for screening a series of synthesized thiadiazole derivatives. This led to the identification of a candidate molecule (S21) with a remarkable inhibitory activity against Hippo as well as Wnt and TGF beta pathways. S21 suppressed cancer cell ability to undergo EMT, to proliferate, and to become drug resistant. Investigation of the underlying mechanism led to the finding that S21 induces phosphorylation of Mst1 and Lats1, two tumor suppressor kinases that negatively regulate Hippo signaling. Since EMT is also known to play a key role in organ fibrosis, the effects of S21 on expression of the associated markers including collagen-I, fibronectin and vimentin, in comparison to the well described anti-fibrotic drug Pirfenidone, was investigated. The data demonstrated that S21 has superior inhibitory activity on pro-fibrotic pathways and markers than Perfinidone, suggesting that this compound may have great potential for the treatment/prevention of fibrotic diseases. The data suggests that certain thiadiazole derivatives may represent the first pan-EMT inhibitors and thus have applications as anti-cancer and anti-fibrotic drug candidates.

In certain embodiments, the compounds disclosed herein are activators of the tumor suppressor kinase AMPK suggesting that these type of compounds may have applications for treating not only EMT associated pathologies such as cancer and fibrosis, but also other diseases associated with AMPK. The compounds may act as activators of tumor suppressor kinases (AMPK and Mst/Lats), leading to activation of the GSK3 beta associated degradation complex, which is responsible for degradation of TAZ and other EMT inducing transcription factors.

Compounds

Disclosed herein are thiadiazole derivatives, and pharmaceutically acceptable salts and esters thereof, having a structure of:

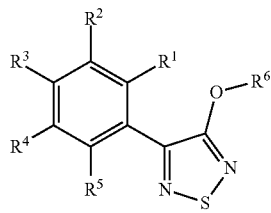

wherein each of $R^1$-$R^5$ is individually selected from H, halogen, optionally substituted alkyl, optionally substituted alkoxy, nitro, sulfonamide, hydroxy, or amino; and $R^6$ is selected from H, optionally substituted alkyl, or optionally substituted aryl.

In certain embodiments, each of $R^1$-$R^5$ is H. In certain embodiments, $R^1$, $R^2$ and $R^5$ are each H, and $R^3$ and $R^4$ are each not H (e.g., $R^3$ and $R^4$ are each halogen). In certain embodiments, $R^1$, $R^2$, $R^4$ and $R^5$ are each H, and $R^3$ is not H (e.g., $R^3$ is halogen, optionally substituted alkyl, or optionally substituted alkoxy). In certain embodiments, $R^3$ and $R^4$ are each halogen, particularly Cl. In certain embodiments, $R^3$ is halogen, particularly Cl. In certain embodiments, $R^3$ is optionally substituted alkyl such as $C_1$-$C_6$ alkyl (e.g., haloalkyl). In certain embodiments, $R^3$ is optionally substituted alkoxy such as $C_1$-$C_6$ alkoxy. In certain embodiments, at least one of $R^3$ and $R^4$ is independently selected from halogen, alkyl, haloalkyl, nitro, —$NH_2$, alkylamino, sulfonamide, or alkoxy.

In certain embodiments, $R^6$ is a hydroxyalkyl, particularly a hydroxyalkyl having a structure of —$(CH_2)_a$—OH, wherein a is 1 to 6, more particularly 4. In certain embodiments, $R^6$ is a hydroxyaryl having a structure of —$C_6H_4$—OH. In certain embodiments, $R^6$ is an aminoalkyl having a structure of —$(CH_2)_a$-amino, wherein a is 1 to 6, more particularly 4. In certain embodiments, $R^6$ is a sulfonamidealkyl having a structure of —$(CH_2)_a$-sulfonamide, wherein a is 1 to 6, more particularly 4. In certain embodiments, $R^6$ is a cyanoalkyl having a structure of —$(CH_2)_a$—CN, wherein a is 1 to 6, more particularly 4. In certain embodiments, $R^6$ is an haloalkyl having a structure of —$(CH_2)_a$-halo, wherein a is 1 to 6, more particularly 4.

Contemplated herein are any combinations of $R^1$-$R^6$ groups disclosed above.

In one embodiment the thiadiazole derivative (compound C19) has the structure:

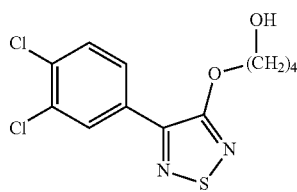

In one embodiment the thiadiazole derivative (compound S21) has the structure:

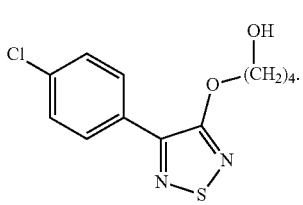

Thiadiazoles (3a-e) were synthesized in three steps from commercially available aldehydes 1a-e (Scheme 1). Treatment of the aldehydes with lithium bis(trimethylsilylamide) (LiHMDS) and acetone cyanohydrin provided the aminonitriles, which are converted to thiadiazole chlorides 2a-e upon treatment with sulfur monochloride. Substitution of chlorides 2a-e with the sodium alkoxide of 1,4-butanediol yielded desired thiadiazoles 3a-e.

Scheme 1. Synthesis of Thiadiazoles 3a-e.

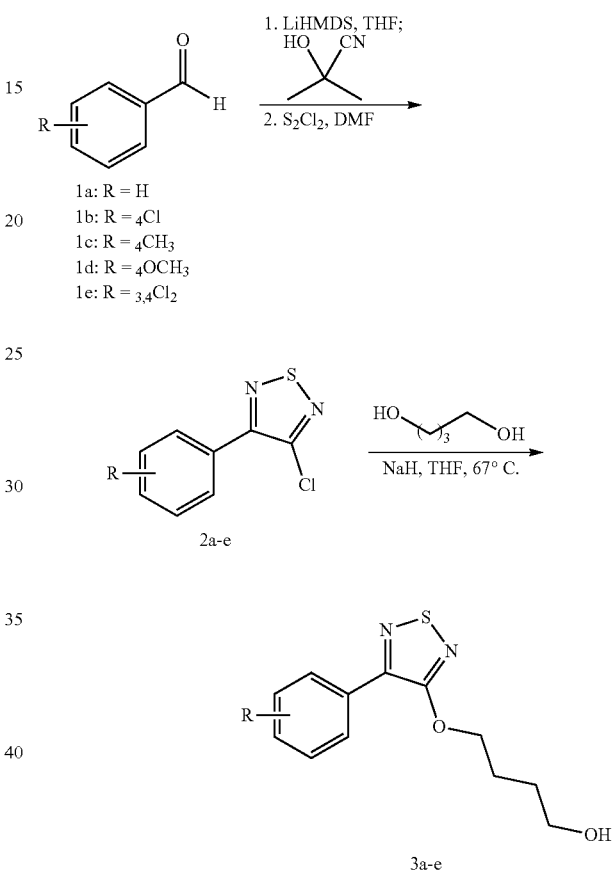

1a: R = H
1b: R = $_4$Cl
1c: R = $_4$CH$_3$
1d: R = $_4$OCH$_3$
1e: R = $_{3,4}$Cl$_2$

Compound 1b is S21.
Compound 1e is C19.

Bioisosteres of the alcohol side chain can be prepared by substitution reactions on either the synthesized thiadiazole (2) or commercially available thiadiazole chloride 3, to provide various thiadiazole ethers (4 and 5, Scheme 2). Ullman reaction conditions are utilized to generate the hydroquinone-derived products (4h and 5h).

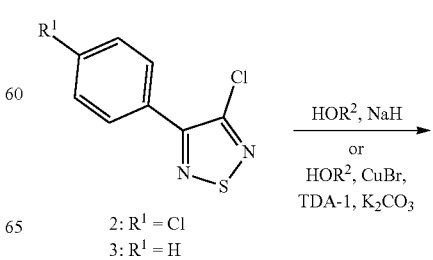

2: $R^1$ = Cl
3: $R^1$ = H

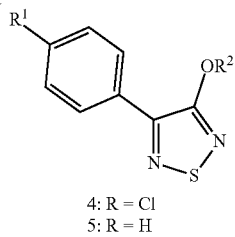

4: R = Cl
5: R = H

4a/5a: $R^2 = (CH_2)_nOH$
4b/5b: $R^2 = (CH)_4NHCOR^3$
4c/5c: $R^2 = (CH)_4NHSO_2R^3$
4d/5d: $R^2 = (CH)_4SONHR^3$
4e/5e: $R^2 = (CH)_4NHCONH_2$
4f/5f: $R^2 = (CH)_4CN$
4g/5g: $R^2 = (CH)_4CHF_2$
4h/5h: $R^2 = C_6H_4OH$

The aromatic side chain can be modified from commercially available aldehydes (6) to examine how electronic deficiency (7a-g), electron enhancement (7h-7n), and steric strain (7o-7q) affect bioactivity (Scheme 3).

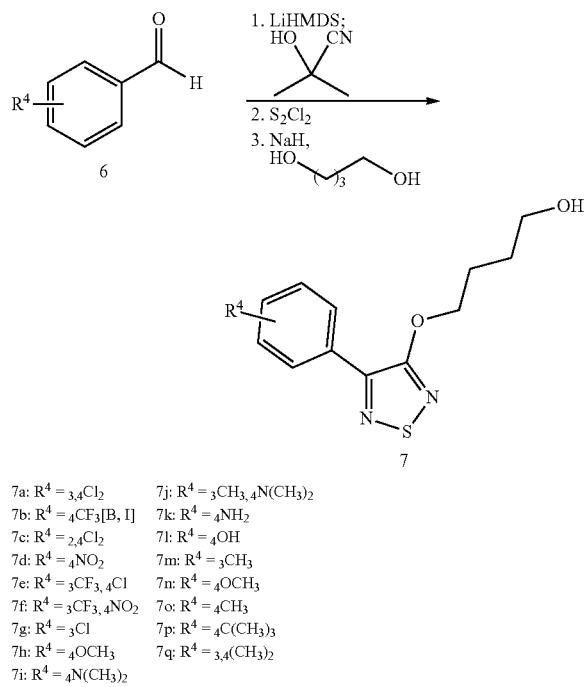

7a: $R^4 = {}_{3,4}Cl_2$
7b: $R^4 = {}_4CF_3[B, I]$
7c: $R^4 = {}_{2,4}Cl_2$
7d: $R^4 = {}_4NO_2$
7e: $R^4 = {}_3CF_3, {}_4Cl$
7f: $R^4 = {}_3CF_3, {}_4NO_2$
7g: $R^4 = {}_3Cl$
7h: $R^4 = {}_4OCH_3$
7i: $R^4 = {}_4N(CH_3)_2$
7j: $R^4 = {}_3CH_3, {}_4N(CH_3)_2$
7k: $R^4 = {}_4NH_2$
7l: $R^4 = {}_4OH$
7m: $R^4 = {}_3CH_3$
7n: $R^4 = {}_4OCH_3$
7o: $R^4 = {}_4CH_3$
7p: $R^4 = {}_4C(CH_3)_3$
7q: $R^4 = {}_{3,4}(CH_3)_2$

Pharmaceutical Compositions and Methods of Use

In certain embodiments, the compounds disclosed herein may be used for treating epithelial-mesenchymal transition (EMT)-associated disorders. Illustrative EMT features associated with cancer include metastasis enhanced proliferation and resistance to treatment. Illustrative cancers include skin cancer, breast cancer, colon cancer, lung cancer, or blood cancer. Illustrative EMT-associated fibrotic disorders include those that affect the liver, lung, kidney, heart, and the skin, amyotrophic lateral sclerosis, multiple sclerosis, tuberous sclerosis, thrombosis, neurofibromatosis, neuro-inflammation, inflammatory pain, and neuropathic pain.

In certain embodiments, the compounds disclosed herein may be co-administered with other anti-cancer agents for treating metastatic and/or drug-resistant cancers.

The compounds disclosed herein may have applications in treating and/or preventing various disorders associated with AMPK including cancer, type 1 diabetes, type 2 diabetes, metabolic syndrome, atherosclerosis, dyslipidemia, mitochondrial disorders, sarcopenia, obesity, hypertension, cerebral ischemia, cognitive defect Alzheimer's disease, Parkinson's disease, Huntington's disease, schizophrenia, Friedrich's Ataxia, metabolic syndrome, atherosclerosis, dyslipidaemia, mitochondrial disorders, sarcopenia, obesity, hypertension, cerebral ischemia, organ fibrosis, amyotrophic lateral sclerosis, multiple sclerosis, tuberous sclerosis, neurofibromatosis, neuro-inflammation, inflammatory pain, neuropathic pain, epilepsy, virus infection (HIV, cytomegalovirus and hepatitis C), and aging associated disorders.

Another aspect of the disclosure includes pharmaceutical compositions prepared for administration to a subject and which include a therapeutically effective amount of one or more of the compounds disclosed herein. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface-active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids. Particular disclosed compounds possess at least one basic group that can form acid-base salts with acids. Examples of basic groups include, but are not limited to, amino and imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid.

Certain compounds include at least one acidic group that can form an acid-base salt with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions also can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl) amine, 2-hydroxy-tert-butylamine, tris(hydroxymethyl) methylamine, N,N-dimethyl-N-(2-hydroxyethyl)amine, tri-(2-hydroxyethyl)amine and N-methyl-D-glucamine. For additional examples of "pharmacologically acceptable salts," see Berge et al., *J. Pharm. Sci.* 66:1 (1977).

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675, 189).

The pharmaceutical compositions of the disclosure typically are sterile and stable under sterile conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, dog, sheep, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.25 mg/kg body weight to about 250 mg/kg body weight, such as about 1.0 mg/kg to about 100 mg/kg body weight, or about 5 mg/kg to about 50 mg/kg body weight.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, intraosseous, or intranasal delivery versus intravenous or subcutaneous or intramuscular delivery. Dosage can also be adjusted based on the release rate of the administered formulation, for example, of an intrapulmonary spray versus powder, sustained release oral versus injected particulate or transdermal delivery formulations, and so forth.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the compounds described herein. In one example, this component is formulated in a pharmaceutical preparation for delivery to a subject. The compound is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

EXAMPLES

Synthesis of 4-((4-(3,4-dichlorophenyl)-1,2,5-thiadiazol-3-yl)oxy)butan-1-ol (3e)

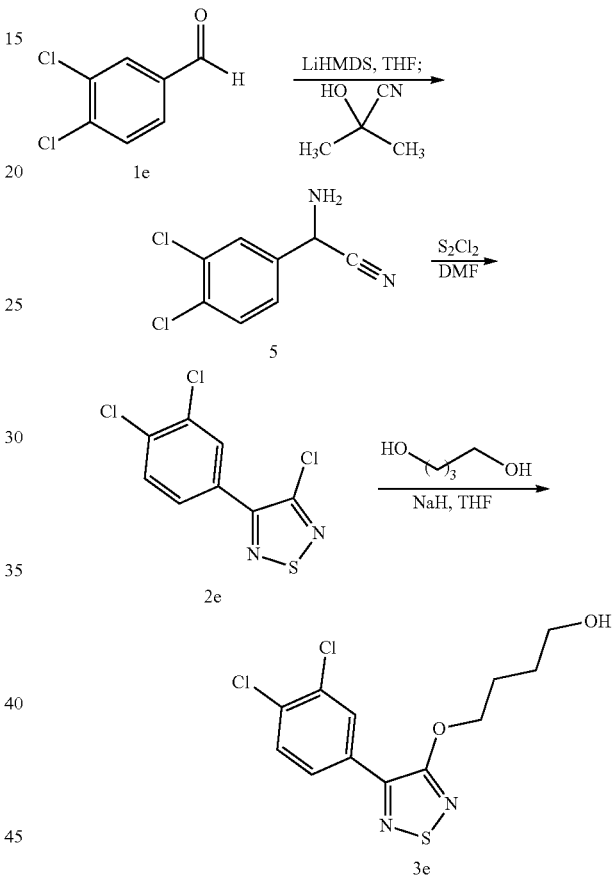

Synthesis of
2-amino-2-(3,4-dichlorophenyl)acetonitrile (5)

To a solution of 3,4-dichlorobenzaldehyde (0.583 g, 3.33 mmol) in anhydrous THF (12 mL) at −40° C. was added lithium bis(trimethylsilyl)amide (LiHMDS, 1.0 M in THF, 5.00 mL, 5.00 mmol) dropwise by syringe. The reaction was let warm to ambient temperature and let stir for 4 h. To the reaction mixture was added acetone cyanohydrin (0.610 mL, 6.68 mmol) and let stir (16 h). The reaction was treated with saturated aqueous $NaHCO_3$ (10 mL), extracted with ethyl acetate (5×20 mL), dried over anhydrous sodium sulfate, filtered, and concentrated. Purification by column chromatography (30% ethyl acetate/hexanes) to afford 501 mg (2.49 mmol, 75% yield) of 2-amino-2-(3,4-dichlorophenyl)acetonitrile (5). TLC $R_f$ 0.19 (20% ethyl acetate/hexanes); $^1$H NMR (60 MHz, CDCl3): δ 7.64-7.62 (m, 1 H), 7.42-7.37 (m, 2 H), 4.89 (s, 1 H), 2.14 (s, 2 H) ppm.

Synthesis of 3-chloro-4-(3,4-dichlorophenyl)-1,2,5-thiadiazole (2e)

To a suspension of 2-amino-2-(3,4-dichlorophenyl)acetonitrile (0.116 g, 0.577 mmol) in DMF (0.7 mL) at 0° C. was added sulfur monochloride (0.150 mL, 1.86 mmol) dropwise by syringe. The reaction mixture was warmed to ambient temperature and let stir 18 h. The reaction mixture was quenched with ice-cold water (1 mL) and filtered. The eluent was diluted with water (5 mL), extracted with $CH_2Cl_2$ (3×10 mL), and the combined organic layers were dried over anhydrous magnesium sulfate, filtered, and concentrated. Purification by column chromatography (hexanes) to afford 82.7 mg (0.310 mmol, 54% yield) of 3-chloro-4-(3,4-dichlorophenyl)-1,2,5-thiadiazole (2e) as a white solid. TLC $R_f$ 0.26 (hexanes); $^1$H NMR (60 MHz, CDCl3): δ 8.08 (d, 1 H, J=2.0 Hz), 7.92 (d, 0.3 H, J=2.0 Hz), 7.78 (d, 0.7 H, J=2.0 Hz), 7.61 (s, 0.7 H), 7.47 (s, 0.3 H) ppm.

Synthesis of 4-((4-(3,4-dichlorophenyl)-1,2,5-thiadiazol-3-yl)oxy)butan-1-ol (3e)

To a suspension of sodium hydride (60% in oil, 0.0246 g, 0.615 mmol) in anhydrous THF (0.6 mL) at 0° C. was added butane-1,4-diol (27.0 μL, 0.306 mmol) dropwise by syringe. The reaction mixture was heated to reflux and let stir for 1 h. The reaction was cooled to ambient temperature and a solution of 3-chloro-4-(3,4-dichlorophenyl)-1,2,5-thiadiazole (2e, 0.0381 g, 0.143 mmol) in anhydrous THF (0.6 mL) was added dropwise by syringe. The reaction mixture was heated back to reflux and let stir 18 h. The reaction mixture was cooled to ambient temperature, treated with saturated aqueous sodium bicarbonate (1 mL) and concentrated under reduced pressure to remove the THF. The residual aqueous mixture was diluted with saturated aqueous sodium bicarbonate (5 mL) extracted with CH2Cl2 (3×5 mL), and the combined organic phases were dried over Na2SO4, filtered, and concentrated. Purification by column chromatography (30% ethyl acetate/hexanes) to give 0.0231 g (0.0724 mmol, 51% yield) of 4-((4-(3,4-dichlorophenyl)-1,2,5-thiadiazol-3-yl)oxy)butan-1-ol (3e) as a white solid. TLC $R_f$ 0.11; $^1$H NMR (60 MHz, CDCl3): δ 8.29 (d, 1 H, J=1.9 Hz), 8.09 (d, 0.4 H, J=2.0 Hz), 7.95 (d, 0.6 H, J=6.2 Hz), 7.59 (s, 0.6 H), 7.45 (s, 0.4 H), 4.57 (t, 2 H, J=6.2 Hz), 3.76 (t, 2 H, J=5.9 Hz), 2.04-1.76 (m, 2 H), 1.48-1.13 (m, 2 H) ppm.

Screening for Small Molecules Inhibitors of Hippo Pathway

A TEAD luciferase reporter system was used as a readout for Hippo signaling, to screen a series of thiadiazole derivatives synthesized in our laboratory. For this, 293 cells transfected with the reporter construct were incubated in the absence or the presence of individual compounds at 10 μM concentration each for 24 hours. Proteins were then extracted and used as a source of enzyme of luciferase activity. The data presented in FIGS. 1A and 7 shows that most of the tested compounds had either no or weak effects on the activity of this enzyme (by comparison to the control (C). However, the compound #S21 (S21), the structure of which is shown in FIG. 2B, exerted the strongest inhibition. This effect was specific since S21 did not inhibit the activity of luciferase driven by the CMV promoter (FIG. 2C).

Figure 2:
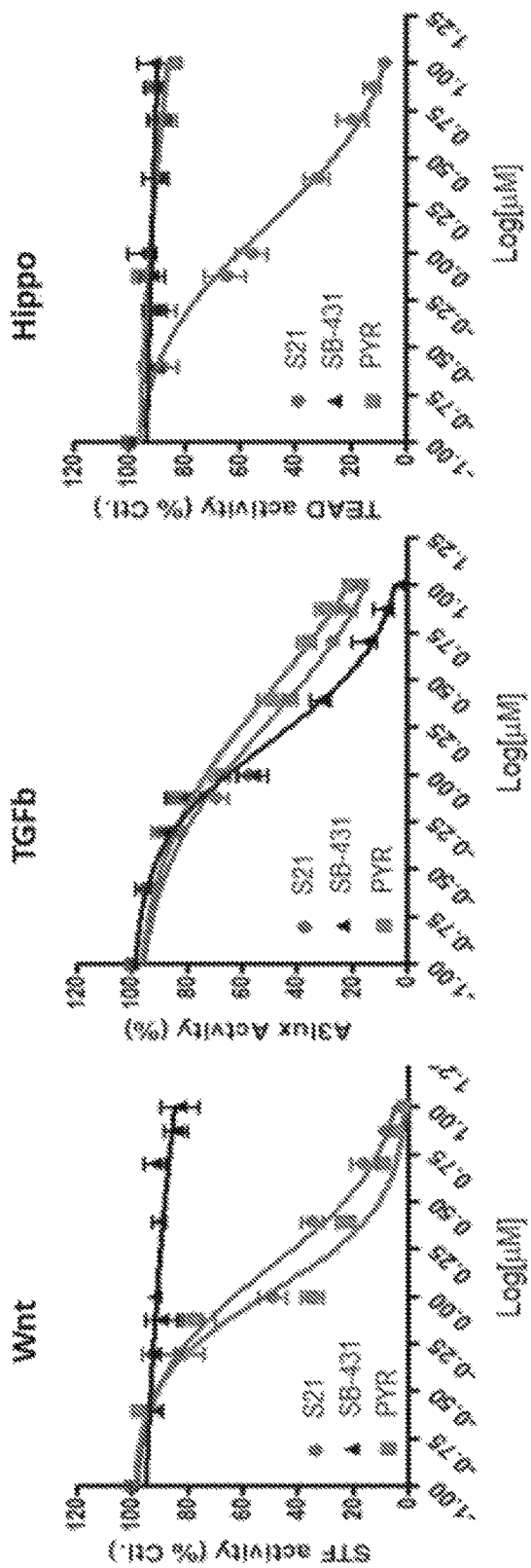
FIG. 2. S21 as a common inhibitor of Wnt, TGF beta and Hippo. 293 cells were transfected with luciferase reporters corresponding to each pathway and then exposed to S21, the Wnt inhibitor Pyrvinium (PYR) or the TGF beta inhibitor SB-431 at the indicated concentrations. After 24 hours, the cells were lysed and luciferase activity measured. Data represent average of three replicates ±SE.

The effect of S21 was also tested on Wnt and TGF beta signaling and as shown in FIG. 2, this compound remarkably inhibited both pathways. By comparison, none of Wnt or TGF beta inhibitors had affected the Hippo pathway reporter. This suggests that S21 may represent a unique candidate molecule to target simultaneously the Hippo, Wnt and TGF beta pathways.

Putative Mechanism(s) by which S21 Function

Figure 3B:
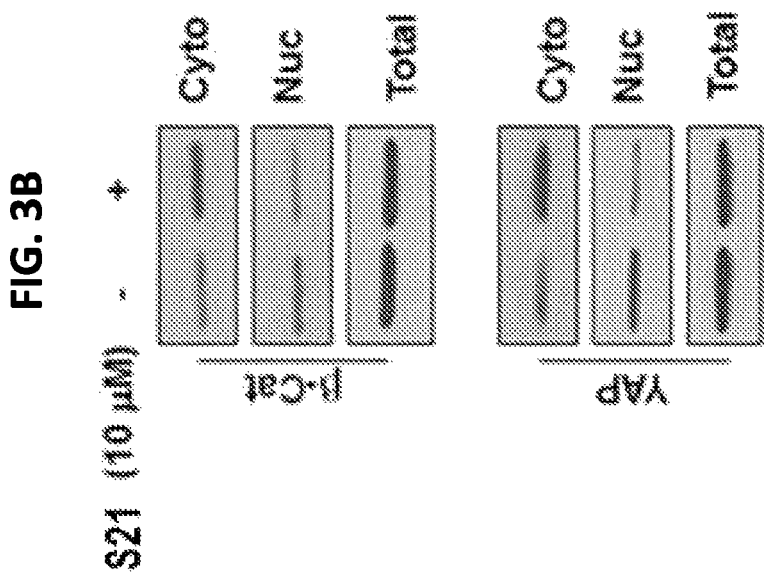
FIGS. 3A-3B. Effect of S21 on key elements of the Hippo pathway. Western blot analysis was carried out to determine the effect of S21 on expression and phosphorylation of MST/Lats (FIG. 3A) and nucleocytoplasmic localization of YAP and beta catenin (FIG. 3B).
Figure 3A:
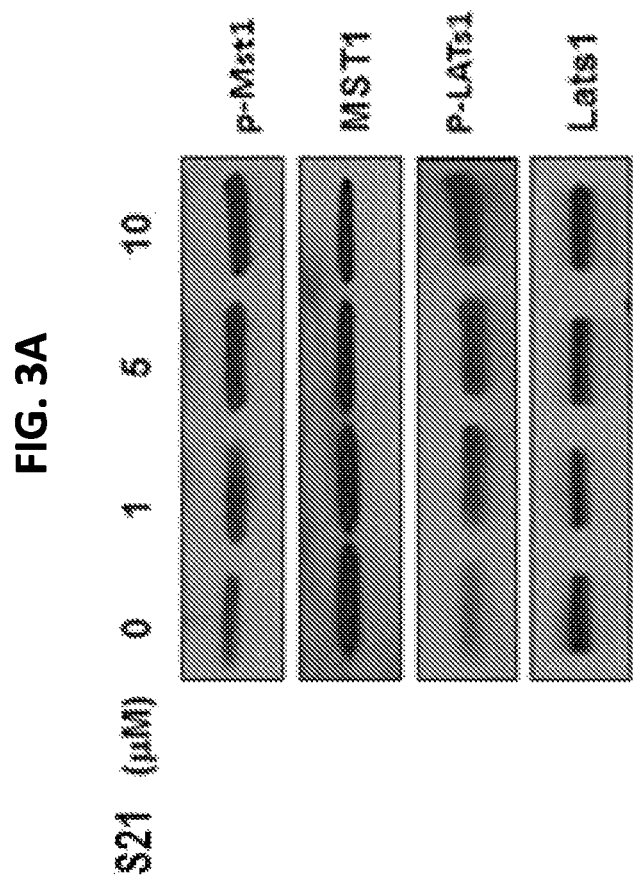

To gain insights into the mechanism(s) by which S21 inhibits the Hippo pathway, its effect on activation of the core kinases MST1 and Lats1 was analyzed. As shown in FIG. 3A, this compound induced phosphorylation of both enzymes in a dose-dependent manner. In addition, S21 reduced nuclear localization and enhanced cytoplasmic levels of both YAP and beta catenin (FIG. 3B), a finding that is in line with suppression of the transactivating activities of these two transcription factors by S21 (FIG. 2). These results provide insights into the possible molecular mechanism by which S21 inhibits the Hippo pathway, which is through activation of the tumor suppressor kinases Mst1 and Lats1.

Figure 4A:
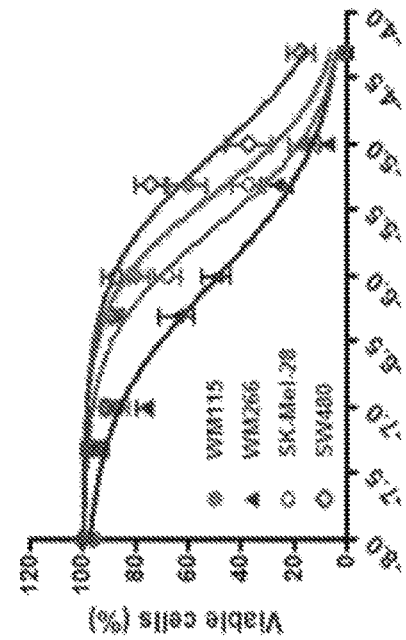
FIGS. 4A-4D. Inhibition of EMT, cell migration, proliferation and resistance to therapy by S21.
Figure 4C:
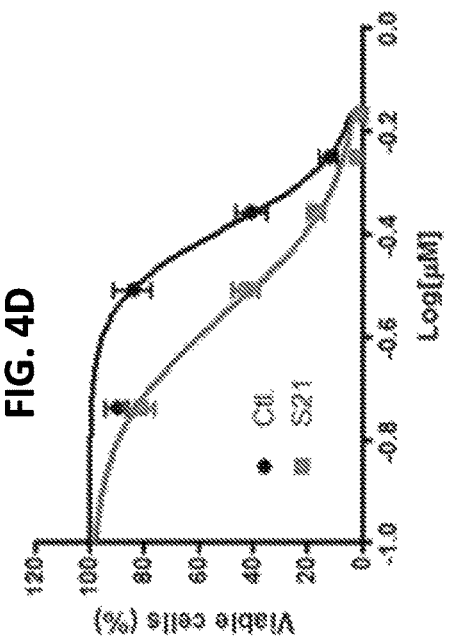
Figure 4B:
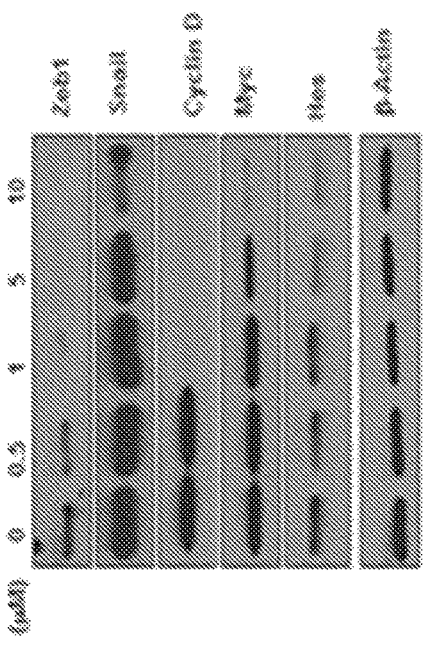
Figure 4D:
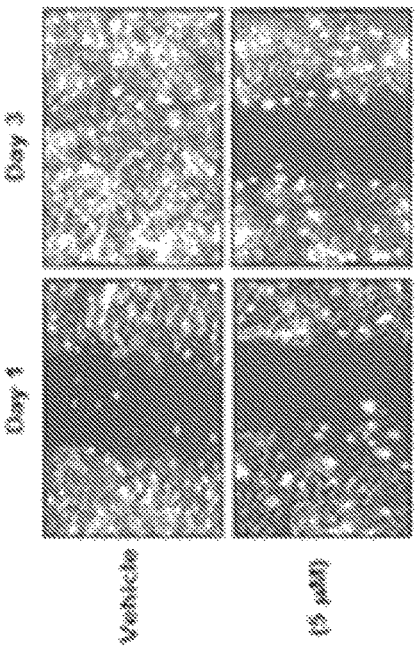

Effect of S21 on EMT, Cancer Cell Migration, Proliferation and Resistance to Therapy It was found that S21 strongly inhibits expression of the EMT-associated gene Zeb1 and to a lesser extent that of Snail (FIG. 4A). The levels of downstream targets genes such as Cyclin D, Myc and Hes were also reduced in cells exposed to S21. This, in addition to the finding that cell migration was strongly inhibited by this compound (FIG. 4B), suggests that it may represent a potent EMT inhibitor. The anti-proliferative action of S21 was demonstrated using three melanoma and one colon cancer cell lines (FIG. 4C). Interestingly, it was found that the metastatic melanoma cell line WM266 responded better to S21 than its non-metastatic counterpart WM115, suggesting that this compound may act preferentially on metastatic cancer cells. Since the development of resistance has been shown to be associated with EMT, whether S21 affects this process as well was also investigated. The data presented in FIG. 4D shows that melanoma cell response to doxorubicin was significantly enhanced in the presence of this compound. Future studies will be needed to elucidate the underlying mechanism.

Effect of S21 Versus Pirfenidone on Activation of Profibrotic Pathways and Expression of Fibrosis Markers Fibrosis is a biological process that leads to the formation of excess fibrous material and replacement of tissue parenchyma with scar tissue. It affects millions of individuals worldwide, and is a leading cause of organ failure. Abnormal and exaggerated deposition of extracellular matrix is the hallmark of many fibrotic diseases, including systemic sclerosis and pulmonary, liver, and kidney fibrosis. The spectrum of affected organs, the usually progressive nature of the fibrotic process, the large number of affected persons, and the absence of effective treatment pose an enormous challenge for treating fibrotic diseases. From the mechanistic point of view, activated fibroblasts represent the key cellular players in the initiation of fibrosis due to their ability to secrete various extracellular factors among which fibronectin and collagen are the most described. Recent evidence indicated that stressed epithelial cells may also contribute to secretion of pro-fibrotic factors.

Figure 5:
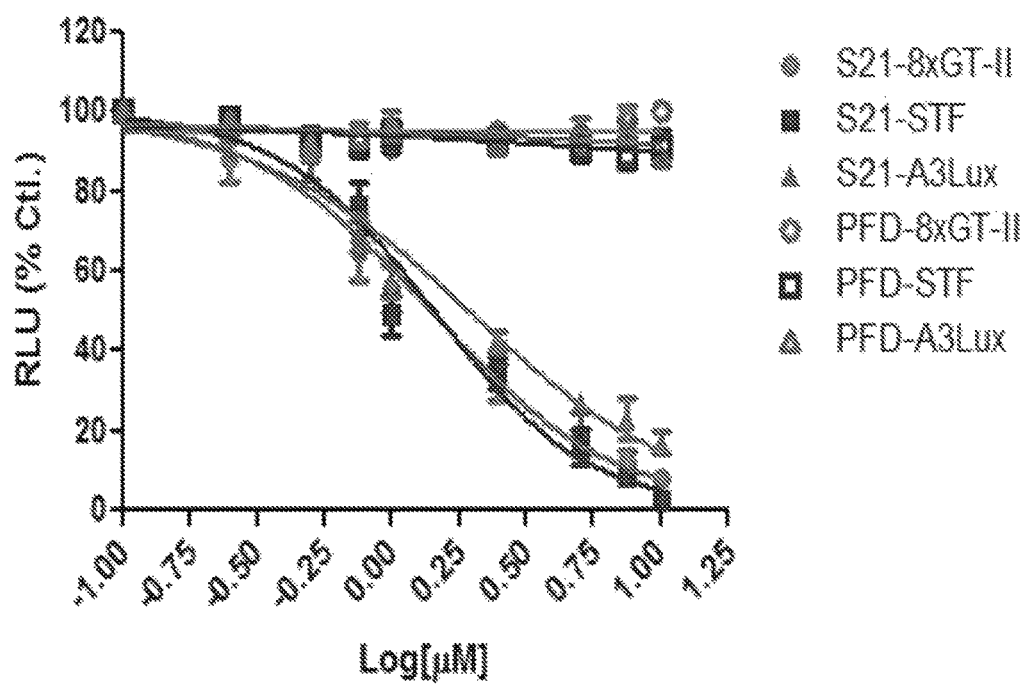
FIG. 5. Effect of S21 versus Pirfenidone on activity of Wnt, TGF beta and Hippo reporters. 293 cells were transfected with luciferase reporters corresponding to the three pathways and then incubated with the indicated concentration of S21 or Pirfenidone for 24 hours. Luciferase activity was measured in the protein extract. Each point represents average of three determinations ±SE.

Despite many years of research, the pathogenesis of fibrosis remains obscure and a cure is still elusive. Since EMT is now recognized as an integral part of tissue fibrosis, targeting the associated pathways should attenuate disease progression. The effect of S21 versus Pirfenidone, a widely used drug for fibrotic conditions, on activation of the EMT associated pathways (TGF beta, Wnt and Hippo) was compared. As indicated in FIG. 5, S21 exerted a dose dependent inhibition on the activity of the three reporters while Pirfenidone was without effect. In subsequent experiments, Pirfenidone was tested for up to 100 μM and no inhibition was detected (data not shown).

Figure 6A:
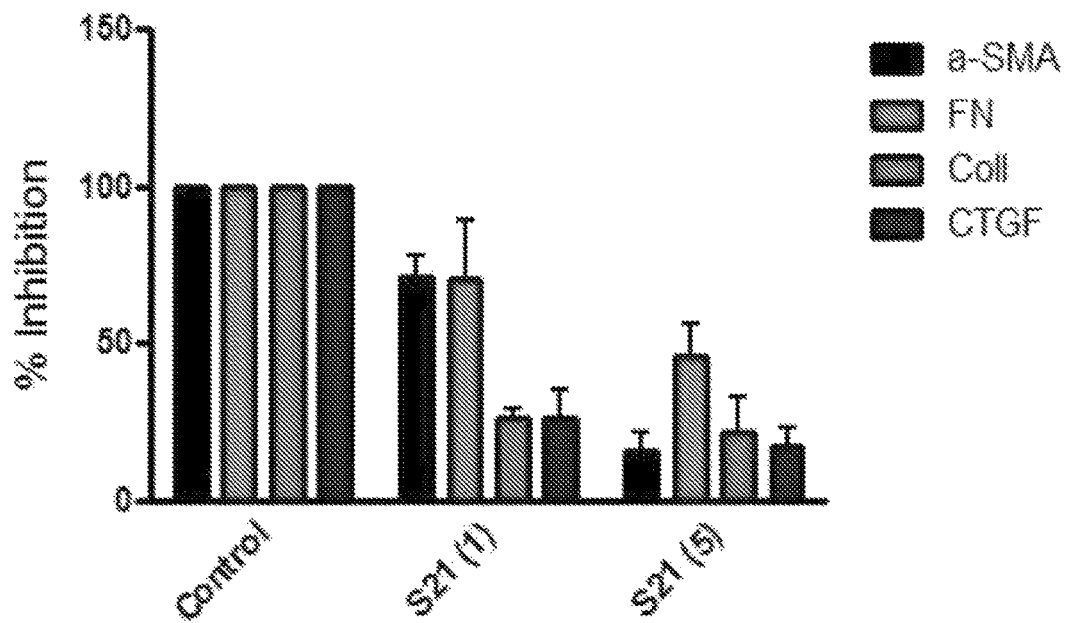
FIGS. 6A-6B. S21 inhibits expression of pro-fibrotic and pro-EMT genes.
Figure 6B:
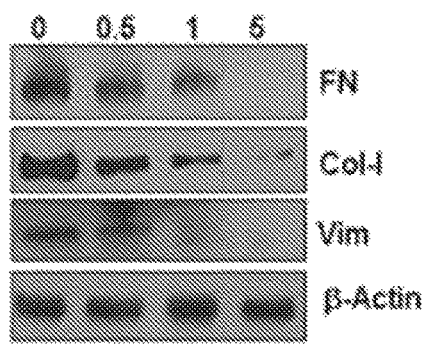

Consistent with the previous data, it was found that exposure of fibroblasts to S21 resulted in a dose dependent decrease in expression of fibrotic markers including Finbronectin, Collagen at the RNA (FIG. 6A) and the protein level (FIG. 6B). These data strongly support potential anti-fibrotic activity of S21.

Overall, it has been shown that S21 inhibits all three EMT pathways (Wnt, TGF beta and Hippo) and by doing so, it inhibited cancer cell migration, proliferation and resistance to therapy. S21 also displayed strong anti-fibrotic activity suggesting that this compound and or its analogs may have applications to treat both cancer and organ fibrosis.

Anticancer Activity of C19 In Vivo

Figure 9B:
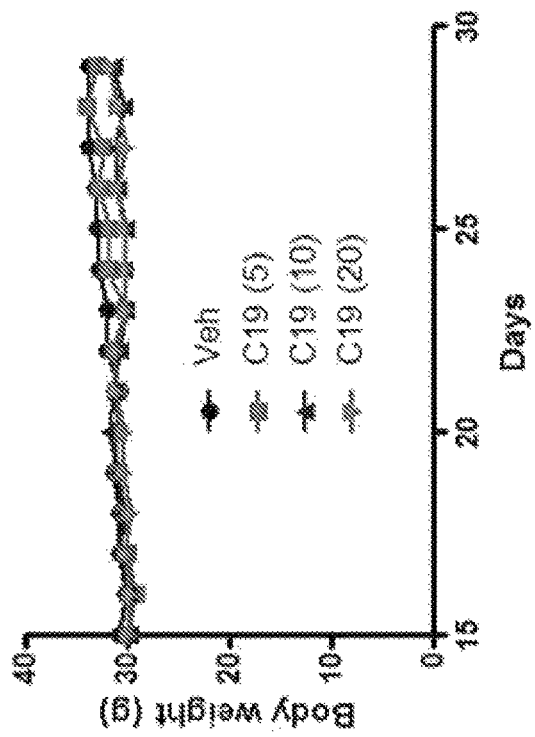
FIGS. 9A-9B. Effect of C19 (mg/Kg) on tumor growth (FIG. 9A) and body weight (FIG. 9B). Data represents 7 replicates ±SE. *p<0.05., **p<0.01.
Figure 9A:
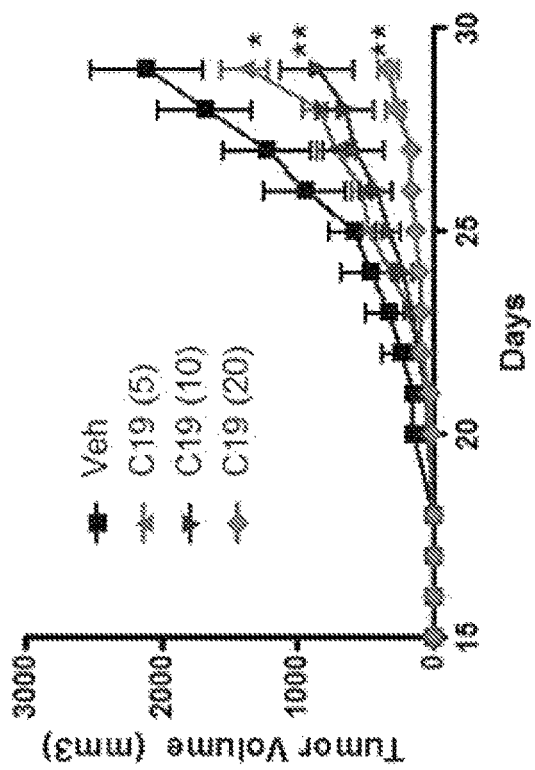

To obtain information regarding the efficacy of C19 in a tumor xenograft mouse model, nude mice (strain CD1) were injected subcutaneously with melanoma cells WM266. After tumors became palpable (~5 mm in diameter), the mice were randomized into control and treatment groups (n=7). The control group was injected intraperitoneally with the vehicle (DMSO 3% in 200 μl of DMEM) and the treatment groups were injected with increasing doses of C19 (in mg/Kg) dissolved in 200 μl of vehicle solution. The animals received 3 injections starting on day 15 and separated by three days. Tumor volumes and body weight were measured on a daily basis. The data presented in FIG. 9A indicate that C19 suppresses tumor growth in a dose dependent manner with 20 mg/Kg inducing about 90% of inhibition. Mice in treatment groups were in good health and their body weight did not change significantly compared to controls (FIG. 9B). No signs of toxicity or death were reported throughout the experiment.

C19 as a Potent Activator of AMPK

Investigation of the mechanism by which C19 exert its activity led to the discovery that, in addition to its effect on MST/Lats, this compound acts as a potent activator of the metabolic enzyme and tumor suppressor kinase AMPK (FIG. 10). C19 induced phosphorylation (activation) of AMPK in a concentration and time dependent manner (FIGS. 10A and 10B) and its effect was at least 10 times more potent than AICAR, a well-known activator of this enzyme (FIG. 10C). The effect of C19 on AMPK was validated in different cell lines (FIG. 10D) suggesting that this may represent a general phenomenon. This compound also induced phosphorylation of ACC (FIG. 10E) and Ulk1 (FIG. 10F) two downstream targets of AMPK respectively implicated in lipid metabolism and autophagy.

In view of the many possible embodiments to which the principles of the disclosed compound, compositions and methods may be applied, it should be recognized that the illustrated embodiments are only preferred examples of the invention and should not be taken as limiting the scope of the invention.

What is claimed is:

1. A compound, or a pharmaceutically acceptable salt or ester thereof, having a structure of:

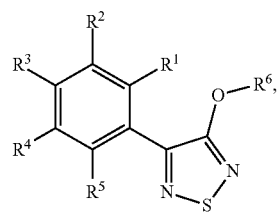

wherein each of $R^1$-$R^5$ is individually selected from H, halogen, optionally substituted alkyl, optionally substituted alkoxy, nitro, sulfonamide, hydroxy, or amino; and $R^6$ is a hydroxyalkyl.

2. The compound of claim 1, wherein each of $R^1$-$R^5$ is H.

3. The compound of claim 1, wherein $R^1$, $R^2$ and $R^5$ are each H, and $R^3$ and $R^4$ are each not H.

4. The compound of claim 1, wherein $R^1$, $R^2$, $R^4$ and $R^5$ are each H, and $R^3$ is not H.

5. The compound of claim 1, wherein $R^3$ and $R^4$ are each halogen.

6. The compound of claim 1, wherein $R^3$ is halogen.

7. The compound of claim 1, wherein, at least one of $R^3$ and $R^4$ is independently selected from halogen, alkyl, haloalkyl, nitro, —$NH_2$, alkylamino, sulfonamide, or alkoxy.

8. The compound of claim 1, wherein $R^6$ is a hydroxyalkyl having a structure of —$(CH_2)_a$—OH, wherein a is 1 to 6.

9. The compound of claim 1, having a structure of:

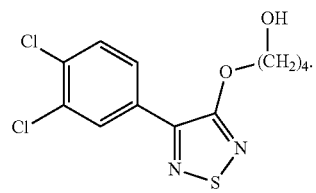

10. The compound of claim 1, having a structure of:

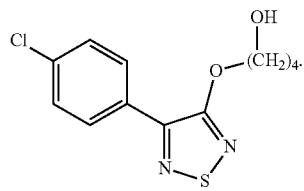

11. A pharmaceutical composition, comprising a therapeutically effective amount of a compound of claim 1, and at least one pharmaceutically acceptable additive.

12. The pharmaceutical composition of claim 11, further comprising at least one additional anti-cancer agent.

13. A compound, or a pharmaceutically acceptable salt or ester thereof, having a structure of:

wherein each of $R^1$-$R^5$ is individually selected from H, halogen, optionally substituted alkyl, optionally substituted alkoxy, nitro, sulfonamide, hydroxy, or amino; and $R^6$ is selected from a hydroxyaryl having a structure of —$C_6H_4$—OH; an aminoalkyl having a structure of —$(CH_2)_a$-amino, wherein a is 1 to 6; a sulfonamidealkyl having a structure of —$(CH_2)_a$-sulfonamide, wherein a is 1 to 6; or a cyanoalkyl having a structure of —$(CH_2)_a$—CN, wherein a is 1 to 6.

14. A compound, or a pharmaceutically acceptable salt or ester thereof, having a structure of:

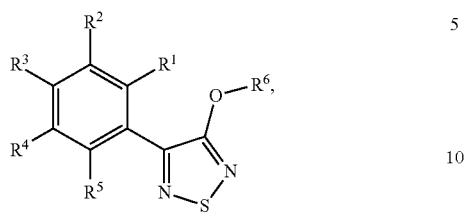

wherein each of $R^1$, $R^2$, and $R^5$ are each individually selected from H, halogen, optionally substituted alkyl, optionally substituted alkoxy, nitro, sulfonamide, hydroxy, or amino; $R^3$ and $R^4$ are each halogen; and $R^6$ is selected from H, optionally substituted alkyl, or optionally substituted aryl.

* * * * *